(12) United States Patent
Berezhnyy et al.

(10) Patent No.: US 9,754,471 B2
(45) Date of Patent: Sep. 5, 2017

(54) ELECTRONIC SWITCH FOR CONTROLLING A DEVICE IN DEPENDENCY ON A SLEEP STAGE

(71) Applicant: KONINKLIJKE PHILIPS N.V., Eindhoven (NL)

(72) Inventors: Igor Berezhnyy, Eindhoven (NL); Pedro Miguel Fonseca, Antwerp (BE); Adrienne Heinrich, Den Bosch (NL); Reinder Haakma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 237 days.

(21) Appl. No.: 14/435,319

(22) PCT Filed: Nov. 4, 2013

(86) PCT No.: PCT/IB2013/059892
§ 371 (c)(1),
(2) Date: Apr. 13, 2015

(87) PCT Pub. No.: WO2014/068537
PCT Pub. Date: May 8, 2014

(65) Prior Publication Data
US 2015/0302722 A1    Oct. 22, 2015

Related U.S. Application Data

(60) Provisional application No. 61/721,540, filed on Nov. 2, 2012.

(51) Int. Cl.
G08B 21/06 (2006.01)
A61B 5/00 (2006.01)
(Continued)

(52) U.S. Cl.
CPC .......... *G08B 21/06* (2013.01); *A61B 5/02405* (2013.01); *A61B 5/04012* (2013.01);
(Continued)

(58) Field of Classification Search
CPC ...................... A61M 2021/0083; A61M 21/00
See application file for complete search history.

(56) References Cited

U.S. PATENT DOCUMENTS

| 8,021,299 B2 | 9/2011 | Miesel et al. | |
| 2002/0080035 A1* | 6/2002 | Youdenko | G04B 23/021 340/573.1 |

(Continued)

FOREIGN PATENT DOCUMENTS

| EP | 1830698 B1 | 9/2007 |
| EP | 1943944 A1 | 7/2008 |

(Continued)

*Primary Examiner* — Laura Nguyen

(57) ABSTRACT

An electronic switch for controlling a device 170 by switching a function of the device at least in dependence on a sleep stage of a human. The switch includes an EEG data interface configured to receive brain activity data from an EEG sensor 120 configured to monitor electrical activity of the brain of the human during a training phase, an EEG sleep classifier 125 configured to classify sleep stages of the human from the received brain activity data, and a body data interface configured to receive body activity data from an alternative sensor 130 configured to monitor a bodily function of the human both during the training phase and during a subsequent usage phase. The alternative sensor is different from the EEG sensor, and the electronic switch further includes an alternative sleep classifier 135 and a machine learning system 140, the machine learning system being configured to train the alternative sleep classifier 135 to classify a sleep stage of the human from the received body activity data, the learning system using sleep stages classified by the EEG sleep classifier 125 and concurrent body activity data (Continued)

300 received from the alternative sensor as training data, wherein in the usage phase, the device 170 is controlled in dependency on sleep stages of the human classified by the alternative sleep classifier 135. A control logic 150 is configured to at least determine that the classified sleep stage is one of a set of particular sleep stages and to switch a function of the device at least in dependency on said determination.

9 Claims, 4 Drawing Sheets

(51) Int. Cl.
    *A61B 5/024*     (2006.01)
    *A61B 5/0476*     (2006.01)
    *A61B 5/08*     (2006.01)
    *A61B 5/11*     (2006.01)
    *A61M 21/00*     (2006.01)
    *G04G 13/02*     (2006.01)
    *A61B 5/04*     (2006.01)
    *G08B 13/181*     (2006.01)

(52) U.S. Cl.
    CPC .......... *A61B 5/0476* (2013.01); *A61B 5/0816* (2013.01); *A61B 5/1118* (2013.01); *A61B 5/4809* (2013.01); *A61B 5/4812* (2013.01); *A61B 5/6892* (2013.01); *A61B 5/7264* (2013.01); *A61M 21/00* (2013.01); *G04G 13/02* (2013.01); *G04G 13/021* (2013.01); *G04G 13/025* (2013.01); *G08B 13/181* (2013.01); *A61B 2562/0247* (2013.01); *A61M 2021/0027* (2013.01); *A61M 2021/0044* (2013.01); *A61M 2021/0083* (2013.01); *A61M 2205/3331* (2013.01); *A61M 2205/502* (2013.01); *A61M 2205/584* (2013.01); *A61M 2230/06* (2013.01); *A61M 2230/10* (2013.01); *A61M 2230/42* (2013.01); *A61M 2230/63* (2013.01)

(56) References Cited

U.S. PATENT DOCUMENTS

| | | | |
|---|---|---|---|
| 2003/0052789 A1* | 3/2003 | Colmenarez | G06K 9/00771 340/575 |
| 2005/0190065 A1* | 9/2005 | Ronnholm | A61M 21/00 340/575 |
| 2007/0015976 A1* | 1/2007 | Miesel | A61B 5/0006 600/301 |
| 2007/0118026 A1 | 5/2007 | Kameyama et al. | |
| 2008/0157956 A1* | 7/2008 | Radivojevic | A61B 5/11 340/531 |
| 2009/0149699 A1 | 6/2009 | Ullmann | |
| 2010/0268477 A1* | 10/2010 | Mueller, Jr. | A61B 5/14532 702/19 |
| 2011/0034811 A1 | 2/2011 | Naujokat et al. | |
| 2011/0230790 A1 | 9/2011 | Kozlov | |

FOREIGN PATENT DOCUMENTS

| | | |
|---|---|---|
| EP | 2263530 A1 | 12/2010 |
| EP | 2278508 A1 | 1/2011 |
| WO | 2006054306 A2 | 5/2006 |
| WO | 2011017778 A1 | 2/2011 |

* cited by examiner

ELECTRONIC SWITCH FOR CONTROLLING A DEVICE IN DEPENDENCY ON A SLEEP STAGE

CROSS-REFERENCE TO PRIOR APPLICATIONS

This application is the U.S. National Phase application under 35 U.S.C. §371 of International Application No. PCT/IB2013/059892, filed on Nov. 4, 2013, which claims the benefit of U.S. Provisional Patent Application No. 61/721,540, filed on Nov. 2, 2012. These applications are hereby incorporated by reference herein.

FIELD OF THE INVENTION

The invention relates to an electronic switch for controlling a device by switching a function of the device at least in dependence on a sleep stage of a human, the switch comprising a body data interface configured to receive body activity data from a sensor configured to monitor a bodily function of the human, and a sleep classifier configured to classify a sleep stage of the human from the received body activity data, wherein the device is controlled in dependence on sleep stages of the human classified by the sleep classifier, and control logic configured to at least determine that the classified sleep stage is one of a set of particular sleep stages, and to switch a function of the device at least in dependence on said determination.

The invention further relates to an alarm clock, a burglar alarm, and an entertainment system.

The invention further relates to a method for controlling a device switching a function of the device at least in dependence on a sleep stage of a human.

The invention further relates to a computer program for controlling a device by switching a function of the device at least in dependence on a sleep stage of a human when the computer program is run on a computer.

BACKGROUND OF THE INVENTION

Sleep is a physiological process that is commonly described in sleep stages. For example, sleep stages may be classified in: wake, light, deep and rapid eye movement (REM) sleep. The sleep stage may be deduced from measurements of brain activity and transition between these stages. Sleep stages can be identified by labeling brain oscillations captured with proper equipment that logs signals from electrodes attached to the skull of a subject. This way of annotating sleep stages is reliable and considered a "golden standard" in the field of sleep medicine.

An automated detection that a human sleeps, and in particular, automated classification of the particular sleep stage he/she is in, has many applications. For sleep monitoring, in particular, ambulatory and/or unobtrusive sleep monitoring, in particular, home sleep monitoring, the use of an electroencephalogram (EEG) sensor configured to monitor electrical activity of the brain of the human which would be needed to detect sleep from brain activity is considered disadvantageous. An EEG sensor is worn on the head, e.g., in the form of a head cap or head band, and obstructs natural sleep.

Detecting sleep and/or sleep stages could be done using sensors other than the EEG sensors, e.g., using a sensor configured to monitor a bodily function of the human. Such sensors are potentially more comfortable for the user. For example, a non-contact sensor, that detects a bodily function without being in contact with the user disturbs sleep only slightly and is therefore comfortable. If a contact sensor is not wanted or is not possible, it is preferred to use a sensor that is not connected to the head and/or not connected to another device using wires, e.g., a wireless actiometer configured for wearing around a wrist or ankle.

However, sleep classification from a sensor configured to monitor a bodily function of the human lacks accuracy if that sensor is not an EEG sensor configured to monitor electrical activity of the brain worn in direct contact or close proximity to the upper part of the human head covering the brain.

US 20080157956A1 discloses a method where sleep sensor signals are obtained to a mobile communication device from sensor devices. The mobile communication device checks the sleep sensor signals for a sleep state transition, determines the type of the sleep state transition, forms control signals based on the type of the sleep state transition and sends the control signals to at least one electronic device.

U.S. Pat. No. 8,021,299B2 discloses to correlate values of a non-polysomnographic (non-PSG) physiological parameter set to polysomnographically (PSG) determined sleep states. The correlated values of the non-PSG parameter set and sleep states may be analyzed, and a relationship between the values and sleep states may be determined. The relationship may allow determination of sleep states for any given patient based on values of the non-PSG physiological parameter set for the patient. The non-PSG physiological parameter set does not include physiological parameters typically required for PSG, such as brain electrical activity (EEG), eye movement (EOG), and jaw or neck muscular activity or tone (EMG); Medical devices, such as implantable medical devices (IMDs) that would generally be unable to monitor such physiological parameters, may apply the relationship to values of the non-PSG physiological parameter set for a patient to identify sleep states of the patient.

US 20110230790A1 discloses a method for operating a sleep phase actigraphy synchronized alarm clock that communicates with a remote sleep database, such as an internet server database, and compares user physiological parameters, sleep settings, and actigraphy data with a large database that may include data collected from a large number of other users with similar physiological parameters, sleep settings, and actigraphy data. The remote server may use "black box" analysis approach by running supervised learning algorithms to analyze the database, producing sleep phase correction data which can be uploaded to the alarm clock, and be used by the alarm clock to further improve its REM sleep phase prediction accuracy.

SUMMARY OF THE INVENTION

Classifying sleep stages using unobtrusive sensors without having any information about the user in question is difficult. Conventionally, a user would receive his sleep classifier having been pre-trained, from factory, based on information from "typical" users. However, due to the differences between users which are especially pronounced for non-EEG features which can be measured unobtrusively, these systems will lack accuracy.

It would be advantageous to have an improved electronic switch for controlling a device by switching on or off a function of the device at least in dependence on a sleep stage of a human.

An electronic switch is provided for controlling a device by switching a function of the device at least in dependence on a sleep stage of a human, the electronic switch comprising an EEG data interface configured to receive brain activity data from an EEG sensor configured to monitor electrical activity of the brain of the human during a training phase, an EEG sleep classifier configured to classify sleep stages of the human from the received brain activity data, a body data interface configured to receive body activity data from an alternative sensor configured to monitor a bodily function of the human both during the training phase and during a subsequent usage phase, an alternative sleep classifier and a machine learning system, the machine learning system being configured to train the alternative sleep classifier to classify a sleep stage of the human from the received body activity data, the learning system using sleep stages classified by the EEG sleep classifier and concurrent body activity data received from the alternative sensor as training data, wherein, in the usage phase, the device is controlled in dependency on sleep stages of the human classified by the alternative sleep classifier, and control logic configured to at least determine that the classified sleep stage is one of a set of particular sleep stages and to switch a function of the device at least in dependency on said determination.

A better and more reliable classification of sleep stages is obtained from sensing brain activity using a contact electrode. Combining the high quality sleep classification with concurrent body activity data received from the alternative sensor, i.e., the high quality sleep classification indicates the sleep stage the person was in at the moment the body activity data was received, give high quality training data. Using the training data, which is specific to the individual, gives higher quality training for the alternative sleep classifier. Thus a sensor and classification with low interpersonal variation, is used to train a classifier that uses a different type of sensor, say a respiratory, heart or actiograph sensor (RHA) sensor and/or a sensor, which has high interpersonal variation.

A major disadvantage of EEG sensors are their obtrusiveness and inconvenience, and multiple attempts were made to deduce sleep states from other vital signs, e.g., respiration, heart and/or actigraphy. Sleep classifying based on bodily functions, i.e., body activity data, such as respiration, heart and/or actigraphy is referred to as RHA sensing. Note that other bodily functions, e.g., body temperature, muscle tension, etc., may also be monitored by an alternative sensor. Body activity data includes physiology-related signs.

Performance of sleep-classification from bodily functions different than EEG, including RHA-based classification systems, is hampered by large cross subject differences in the manifestation of the signals for different sleep stages. The switch can boost the performance of non-EEG classifiers by recording the brain activity with a reference sensor for the 'gold standard' during one or more nights (preferably as unobtrusively as possible), automatically classifying it in terms of sleep stages and using these as the reference to identify user-specific manifestations of sleep stages in signals obtained with more user-friendly sensors. Also RHA suffers from high interpersonal variation.

Particular simple but efficient is an electronic switch which switches the function on or off. The switch may also switch by increasing or decreasing an intensity of the function, e.g., on a scale. For example, the function may be configured with a discrete scale and the switch may move the function to a next level of the scale in dependency on the sleep stage.

In use, the electronic switch has a training phase and a subsequent usage phase, the phases extend over one or more days. For example, the training phase may be a week. During the training phase training data is collected, the training data comprises received body data and corresponding sleep classification data obtained from the EEG sleep classifier. The received body data may be compressed in the training data, for example, by extracting relevant features and discarding the raw data.

Indeed, one of the major obstacles of sleep state estimation from monitored bodily functions, such as RHA-based sleep state estimation systems, lies in large cross-subject variability in the manifestation of sleep states in RHA signals. Having one or more nights of simultaneous recordings of RHA signals next to brain activity (EEG) allows building a better link between sleep states deduced from EEG and their manifestation in RHA signals. Therefore, having a higher-end EEG based system next to an RHA system boosts performance of RHA-based sleep state classifiers, and reduces the effect of inter-subject differences. In fact, the system may even be used to reduce intra-subject differences, such as seasonal changes, for example. The EEG-based system can provide accurate sleep states estimation, when needed, although at the expense of being less comfortable than a contactless RHA system; for example, for occasional recalibration. For example, recalibration may be done according to a schedule, say once or twice every year, or every season. For example, between fall and winter and between spring and summer are suggested as re-calibration moments.

The electronic switch comprises a drift detection unit configured to detect a drift of a statistical measure determined during the usage phase and a reference measure determined during the training phase. The drift may indicate that the sleeping habits of the human have changed to such an extent, that the sleep classification may no longer be accurate. Upon detecting the drift, the drift detection unit may signal the human for recalibration of the alternative sleep classifier. The recalibration unit may be a repeat of the training phase.

The data drift detection unit may uses a statistical unit configured to determine a statistical measure of the received body activity data during the training phase and store it as a reference measure, and to determine the statistical measure of the received body activity data during the usage phase. For example, the statistical unit may compute statistical measures of the body activity data such as, e.g., the average, standard deviation, statistical distance from body activity data used during training, and the like. Once the statistical measure drifts away from previous values, the data drift detection unit signals the need for a recalibration. For example, if the statistical measure differs more than a predetermined percentage from a previous value of the statistical measure which is used as the reference, say during a number of possibly consecutive days, the data drift detection unit signals the user for recalibration. Signaling the user may use a LED or a display, etc.

In an embodiment, the device is only coupled to the human through the switch. For example, the device may be a household appliance. Using the switch, the household appliance may be turned on or off or otherwise controlled during sleep of a user. Instead of turning a function on or off, one may control the function in another way, for example, one may switch to a different function, for example, one may increase or decrease an intensity of lighting or heating. A typical application is to switch off a household appliance, such as a television or lighting, when a user is sleeping; or to turn on a household appliance, such as a burglar alarm, when a user is sleeping; or to turn on a household appliance when a user is near waking up, for example a wake-up light, wake-up alarm, lighting, heating, etc. Using the switch, appliances may be controlled.

The electronic switch may be extended with a clock configured to indicate a current time, e.g., an electronic clock. The electronic switch comprising a clock may switch in dependence on sleep stage and time. Indeed, in an embodiment, the switch comprises a clock configured to indicate a current time, the control logic being configured to switch the function at least in dependence on both the classified sleep stage and the current time. One may refer to such a switch as a time switch (also called timer switch) which is sleep dependent.

In an embodiment, the time switch is configurable with a first switching time-period. The function is switched on or off when both: a current time indicated by the clock is in the first switching period, and the classified sleep stage is one of the set of particular sleep stages. This combination of sleep and time dependency is advantageous for many applications, where the function needs to be switched on not only when a person is sleeping or has reached a particular sleep stage, but also at a particular time.

For some functions, it is important that at some point they are switched on (or off) regardless of the sleep status of the human. To support that, an embodiment of the time switch is configurable to switch the function on or off when a current time indicated by the clock is at the end of the first switching period regardless of the classified sleep stage.

The first time-period is typically in the order of an hour, say half an hour, or two hours. The time switch may be arranged so that the periods indicate a period within a 24 hour day, the period could be repeated on a subsequent day.

In an embodiment, the control logic is configured to defer switching until the classified sleep stage remained in the set of particular sleep stages for a particular time period. For example, the switch may be configurable with a second time period. The control logic may, for example, require the sleeper to remain in a sleep stage that is in the set of sleep stages for at least the second time period. Should the sleeper wake up before the end of the second time period, the switching may be skipped. Interestingly, to avoid adverse training effects in the humans, e.g., the control logic may choose the particular time period randomly, e.g., randomly within the second time period. The second time period is typically less than an hour, say 20 minutes.

Controlling a device by switching on or off a function of the device in dependence on a sleep stage of a human has many applications. A number of example applications are listed below:

For example, the time switch may be used with, or in, an alarm clock comprising a device configured to wake the human, e.g., through audio and/or visual stimuli, wherein the control logic is configured to switch-on the device to wake the human. Once the human reaches a particular sleep stage during the time period, the human is woken up. For example, the human may be required to reach a light sleep stage, such as the N1 or N2 stage. The alarm clock may use two first switching periods. In the first switching period, the human is woken once he reaches N1 sleep (a very light sleep stage). In the subsequent and optional second first switching period, the human is woken once he reached N1 or N2 (both light sleep stages). After the second first switching period, the human may be woken regardless of his sleep stage. The time switch may be arranged to skip a switching period if the human is awake.

Interestingly, a part or the entire switch, say, at least the device configured to wake the human, may be arranged for wearing in a human ear. This has the advantage of waking only the human concerned. A different human sleeping near the human woken by the switch is not woken. The different human may thus use his or her own sleep dependent alarm clock to wake him or her. This is especially advantageous since the switch is trained to an individual user. One may even have an ear piece configured for wearing in a human ear, comprising a head electrode for measuring brain wave data of the human, a sleep classifier configured to classify a sleep stage of the human from the measured brain wave data, and an alarm clock for waking the human in pre-determined sleep stage in a configurable time period. Nevertheless, in a typical embodiment, the switch will be arranged for placement near a bed, say on a bed stand.

For example, the switch may be used in or with a burglar alarm comprising an intrusion sensor for detecting an intrusion of a burglar, a device configured to raise an alarm in response to the intrusion sensor detecting an intrusion, wherein the control logic is configured to switch-on the device configured to raise an alarm. It is a problem for some people that if they go to bed too late, they forget to switch on the alarm system. Using a non-sleep dependent time switch may be inappropriate if those people going to bed at different times. However, by switching on the alarm if the user in the house is asleep, this problem is avoided. The burglar alarm may use a switch that comprises a body data interface configured to receive body activity data from multiple alternative sensors configured to monitor a bodily function of multiple humans both during the training phase and during a subsequent usage phase. In this way, the alarm can ascertain that multiple people are sleeping. This may be combined with a time period. For example, the system may only turn on the alarm in a night period.

The burglar alarm system is activated when all people in the house are asleep. In an extension, part of the security that tracks the motion within a guarded perimeter is only activated when people are asleep, say it is configurable.

As a final example of the many uses of the switch, the switch may be used with or in an entertainment system comprising a device configured to render video, wherein the control logic is configured to switch-off the device configured to render video. For example, such an entertainment system is especially useful in the bedroom. For example, the television may automatically be turned off in case all viewers are asleep.

Whether the switch turns on or off may be configurable. Controlling a device by switching on or off a function may be done by switching on or off the device. Also the set of particular sleep stages may be configurable. For example, they may be chosen from the set {N1, N2, N3, and REM sleep}, we will also refer to REM sleep as N4. For example, to avoid an unpleasant wake-up call, a wake-up call may be avoided in the N3 and N4 stages. For example, to switch off a television, the television may be switched off in the N2, N3, or N4 stages. For example, an alarm may be turned on in the N1 stage or higher. These settings are exemplary. One may use the classification of the American Academy of Sleep Medicine (AASM), but this is not necessary, one may use other classification, e.g., having more or fewer sleep stages.

The EEG sensor is suitable for detecting sleep and/or classifying sleep stages. For example, the EEG sensor may comprise one or more scalp electrodes. The scalp electrodes are arranged to be placed in close proximity or direct contact to the scalp of the human.

Interestingly, classifying sleep from brain activity data is universal. This means that the EEG sleep classifier may be configured, say in factory, to work on any, at least on the majority, of humans. Interpersonal variation in sleep classification from EEG data is small. However, interpersonal variation in sleep classification from other body data is much larger. This means that there is great scope for improving accuracy of sleep classification from other body data using individual data. Automated classification of sleep or sleep stages from EEG data is possible using a variety of machine learning techniques.

One way to make an EEG sleep classifier is to create a set of EEG training data by receiving EEG data and labeling it by hand. Next, a machine learning algorithm is applied to the EEG training data. It is stressed that to use the switch as defined above, human expert intervention to manually label EEG data is not needed.

Suitable machine learning algorithm include, for example, the so-called support vector machine (SVM), which is a classifier that operates in a higher dimensional space and attempts to label given vectors using a dividing hyperplane. The supervised learning method takes a set of training data and constructs a model that is able to label unknown test data. Other suitable algorithms include decision tree learning, including neural network decision tree learning. The result of applying a machine learning algorithm may be improved by first computing predetermined features, such as power spectral density. The same or a different machine learning algorithm used to create the EEG sleep classifier may be used in the machine learning system. The EEG sleep classifier may even be constructed by hand without intervention of a machine learning system. Note that there are many machine learning algorithms, including SVM.

A variety of bodily functions of the human may be measured. Particularly effective are cardiac information, respiratory information and actiograph (movement) information. Note that a single sensor may be used to obtain multiple types of information. For example, a pressure sensor installed in or under a mattress used by the sleeping human records the pressure exerted by the human on the mattress. The pressure sensor is sensitive to movements of the human. If the pressure sensor is sufficiently sensitive it will also respond to breathing and even to heartbeats.

By doing a frequency analysis on the recorded pressure data the above mentioned three types of data may be obtained. Movement is a low frequency part, Respiratory is a medium frequency part, and cardiac information is high frequency. Alternatively, a low-pass, mid-pass and high-pass filter may be used to split the pressure information into three parts. Training by the machine learning system improved when the input data was split into semantically meaningful data. The switch may comprise a unit for deriving cardio, respiratory and/or actinography signals from a pressure sensor.

Note that the body data sensor is used both during the training phase and during a subsequent usage phase. This does not impose a particular additional burden since the body sensor can be made to be much more comfortable than the EEG sensor. Indeed, in an embodiment, the alternative sensor is configured to monitor without direct contact with the human.

The switch collects data received from the alternative sensing system, i.e., the body data, and the classifications made by the EEG sleep classifier and matches them up so that a received body data has a corresponding sleep classification. This training data is highly individualized since the data was obtained from a specific rather than an 'average' human.

The machine learning system trains the alternative sleep classifier to classify a sleep stage of the human from the received body activity data, the learning system using sleep stages classified by the EEG sleep classifier and concurrent body activity data received from the alternative sensor as training data.

In an embodiment, the alternative sleep classifier may already be trained for an average human, but is further trained to fit the specific human. For example, the learning system may be configured to improve the classification of the alternative sleep classifier by modifying the alternative sleep classifier so that the classifying of sleep stages by the alternative sleep classifier matches closer with the classifying of sleep stages by the EEG sleep classifier.

The switch is an electronic device and may be embedded in or as a computer.

A further aspect of the invention concerns a method for controlling a device by switching on or off a function of the device at least in dependence on a sleep stage of a human, the method comprising monitoring electrical activity of the brain of the human during a training phase, classifying sleep stages of the human from the monitored brain activity data by an electronic EEG sleep classifier, monitoring a bodily function of the human both during the training phase and during a subsequent usage phase, training an electronic alternative sleep classifier to classify a sleep stage of the human from the monitored body activity data, the learning system using sleep stages classified by the EEG sleep classifier and concurrent monitored body activity data as training data by a machine learning system, classifying sleep stages of the human from the monitored body activity data by the alternative sleep classifier, determining that the sleep stage classified by the alternative sleep classifier is one of a set of particular sleep stages, and switching on or off a function of a device at least in dependency on said determination.

A method according to the invention may be implemented on a computer as a computer implemented method, or in dedicated hardware, or in a combination of both. Executable code for a method according to the invention may be stored on a computer program product. Examples of computer program products include memory devices, optical storage devices, integrated circuits, servers, online software, etc. Preferably, the computer program product comprises non-transitory program code means stored on a computer readable medium for performing a method according to the invention when said program product is executed on a computer In a preferred embodiment, the computer program comprises computer program code means adapted to perform all the steps of a method according to the invention when the computer program is run on a computer. Preferably, the computer program is embodied on a computer readable medium.

BRIEF DESCRIPTION OF THE DRAWINGS

These and other aspects of the invention are apparent from and will be elucidated with reference to the embodiments described hereinafter. In the drawings.

Figure 1:
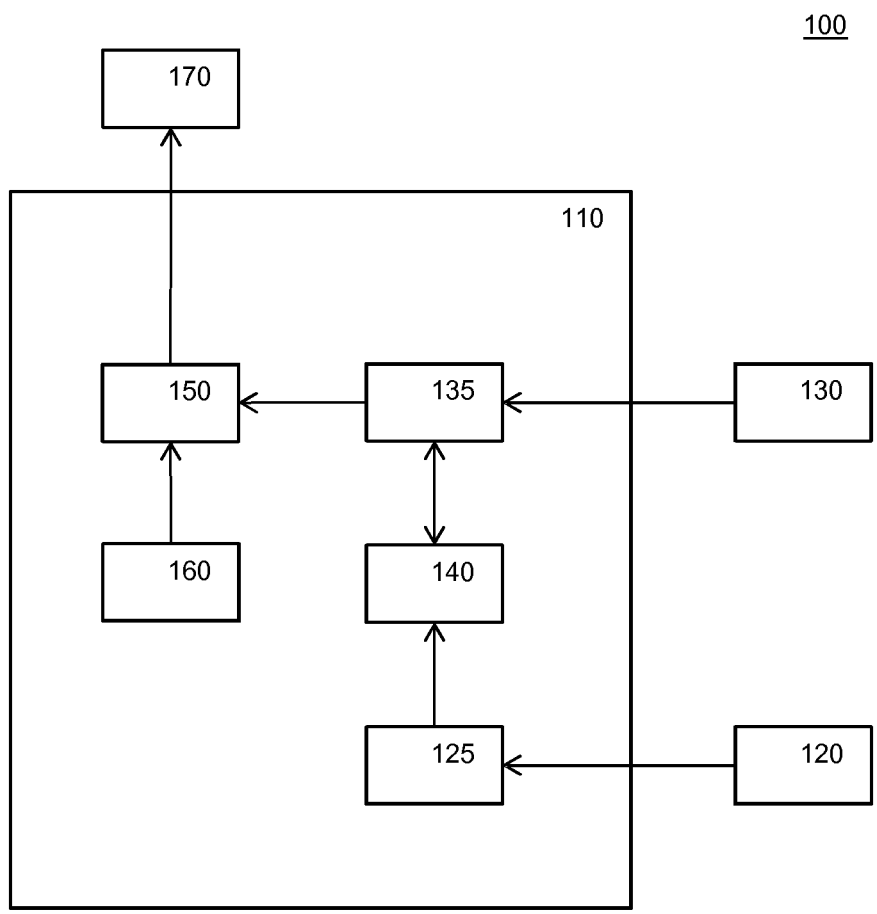
FIG. 1 is block diagram illustrating a sleep stage controlled system.

It should be noted that items which have the same reference numbers in different Figures, have the same structural features and the same functions, or are the same signals. Where the function and/or structure of such an item has been explained, there is no necessity for repeated explanation thereof in the detailed description.

LIST OF REFERENCE NUMERALS 100 a sleep stage controlled system
110 an electronic switch
120 an EEG sensor configured to monitor electrical activity of the brain of the human
125 an EEG sleep classifier configured to classify sleep stages of the human from the received brain activity data
130 an alternative sensor configured to monitor a bodily function of the human
135 an alternative sleep classifier for classifying a sleep stage of the human from the monitored bodily function
140 a machine learning system configured to train the alternative sleep classifier to classify a sleep stage of the human from the received body activity data
150 control logic
160 a clock
170 a device controlled by switch 110
210 sleep classification data
220 wrist actigraphy
230 EEG data
240 a time period showing deep sleep
310 a bed
312 a floor
314 a mattress
320 an EEG sensor
322 an EEG sensor cable
330 a pressure mat
332 a pressure mat cable
350 a buzzer
340 a switch
342 a processor
344 a memory
346 a clock

DETAILED EMBODIMENTS

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described.

FIG. 1 is a schematic block diagram illustrating a sleep stage controlled system 100. FIG. 1 shows an electronic switch 110 and a device 170 controlled by switch 110. The switch may turn the device, or a function thereof, on or off. For example, device 170 may be a device for waking a human, say a buzzer, switch 110 may turn the buzzer on at an appropriate time and in an appropriate sleep stage.

Sleep controlled system 100 further comprises an EEG sensor 120 configured to monitor electrical activity of the brain of the human and an alternative sensor 130 configured to monitor a bodily function of the human. The EEG sensor 120 and the alternative sensor 130 are two different sensors.

The EEG sensor may be a sensor configured for placing at a scalp of a human and may comprise a number of electrodes. The alternative sensor 130 is preferably more comfortable, e.g., being a non-contact sensor, i.e., not in direct contact to the human, and/or a wireless sensor, i.e., not connected to switch 110 through a wire. A good choice for alternative sensor 130 is a pressure sensor placed in or under the mattress. Such a pressure sensor is a non-contact sensor. Such a pressure sensor may be connected to switch 110 through a wire if that is convenient, as it is unobtrusive to the human. Alternative sensor 130 may be an actiograph sensor, for sensing movement of the human. For example, an actiograph sensor may be worn around a wrist or ankle and the like; it is considered more comfortable than an EEG sensor. The alternative sensor 130 may also comprise more advanced system, e.g., a camera, possibly including an infrared filter. From the camera features such as movement, temperature, etc. may be derived.

More in general, it may be desirable to derive features from the raw body data before processing it with a sleep classifier. For example, from a heart sensor, which records the heart activity, features such as heart rate and heart variability, may be derived. Heart rate and heart variability change differently in response to a change in sleep stage. Using heart rate and heart rate variability as two features instead of the raw data allows the machine learning system to learn faster, e.g., the alternative sleep classifier will converge faster towards the performance of the EEG sleep classifier.

Alternative sensor 130 and EEG sensor 120 are shown as connected to switch 110. Switch 110 may be configured so that alternative sensor 130 and/or EEG sensor 120 are detachable. Especially, EEG sensor 120 is preferably detachable from switch 110 since EEG sensor 120 is not used in the usage phase (see below). Alternative sensor 130 and EEG sensor 120 are connected at an interface (not separately shown). In an embodiment, alternative sensor 130 is not an EEG sensor. In an embodiment alternative sensor 130 does not comprise electrodes configured to measure electric brain activity. The bodily function measured by alternative sensor 130 is correlated to sleep and/or sleep stages.

Switch 110 comprises an EEG sleep classifier 125 configured to classify sleep stages of the human from the received brain activity data. EEG sleep classifier 125 is configured before switch 110 is first used. For example, EEG sleep classifier 125 is configured at manufacture, or a user installs a configuration file for EEG sleep classifier 125. The latter has the advantage that EEG sleep classifier 125 may be updated. A combination is possible.

To make EEG sleep classifier 125, one may obtain EEG data from multiple sleeping humans, preferably from multiple backgrounds and across multiple nights and have sleep experts label the EEG data according to a sleep classification system; Next a machine learning system, similar to machine learning system 140 but for EEG data may be used to train EEG sleep classifier 125. Alternatively, EEG sleep classifier 125 may be a rule based expert system using hand-crafted features indicated by the sleep expert.

Switch 110 comprises an alternative sleep classifier 135 for classifying a sleep stage of the human from the monitored bodily function. Alternative sleep classifier 135 may be pre-trained like EEG sleep classifier 125, however its performance is expected to be quite poor. Whereas interpersonal differences are small in so far as sleep classification from EEG data is concerned, the interpersonal differences are much larger when classifying sleep from non-EEG data.

Switch 110 comprises a machine learning system 140 configured to train the alternative sleep classifier 135 to classify a sleep stage of the human from the received body activity data. Machine learning system 140 may be any of a variety of automated machine learning systems similar in construction to machine learning systems used to train a system to classify sleep from EEG data. Note, even though the machine learning system is in principle capable for unsupervised learning, the data may be preprocessed to advantage. For example, frequency analysis may be done, e.g., converting the data to a frequency domain, e.g., a power spectrum. For example, the data may be split using low-, mid- and high-pass filters. For example, the data may be averaged over sequential time intervals, say every 30 seconds, e.g., to reduce noise.

Switch 110 further comprises control logic 150. The control logic receives a sleep classification from alternative sleep classifier 135. Control logic 150 decides if the switching is to be performed or not. Optionally, switch 110 comprises a clock 160, which provides a current time as input to switch 110.

Switch 110 may be configured in many different ways. Switch 110 may be configurable or be configured in a more fixed manner. Switch 110 may simply turn a device off as soon as sleep is detected (any stages), for example, a radiator may be turned off regardless of time, regardless of sleep stage, as long as sleep is detected, or as soon as a specific sleep stage has been detected, e.g., deep or REM sleep. However, using clock 160, more precise configurations are possible.

For example control logic 150, may control controlled device 170 in a sleep dependent manner in a defined time period, i.e., the first switching period; For example, only between 19:00 and 23:00, or 06:30 and 07:00 etc.

In operation, e.g., 'out of the box', switch 110 is started in a training phase. The training phase is at least one night, or at the very least a complete sleep cycle in a night, but more preferably a few days, say a week, or 10 days. Generally, a longer training phase will lead to better training. During the training phase, the user sleeps with both EEG sensor 120 and alternative sensor 130. The EEG data received from EEG sensor 120 is labeled with the appropriate sleep classification. During the training phase, body data from alternative sensor 130 is obtained together with corresponding sleep classification. There may be multiple sets of body data from multiple sensors 130. Also multiple features may be extracted from a single sensor, e.g., RHA data may be extracted from a single pressure sensor.

The training data is used by machine learning system 140 to train alternative sleep classifier 135. This may be done in batch, say at the end of the training phase, or during the accumulation of training data. The end of the training phase may be a fixed moment, say at the end of a week, but machine learning system 140 may also be configured to indicate the quality of training, and may indicate if the quality has reached a minimum quality level, possibly with a minimum duration of the training phase, say of 3 days. For example, when the sleep classification of alternative sleep classifier 135 on data from alternative sensor 130 matches the sleep classification of EEG sleep classifier 125 at least a minimum percentage, say 95%. Preferably, the statistical measure 'Cohen's Kappa' is computed between sleep classification of EEG sleep classifier 125 and alternative sleep classifier 135 and quality is high if it is above a minimum, say above 0.85. At some point, whether at the indication of machine learning system 140 or after a fixed time period, etc., the training phase ends. At that point the usage phase start. The user will then sleep without EEG sensor 120 and only use alternative sensor 130. Alternative sensor 130 may be significantly more comfortable and/or unobtrusive. Alternative sensor 130 may be non-contact and/or wireless and/or not attached to the head but other body parts. Even though the alternative sensor 130 does not sense the EEG data, but other data which has much larger interpersonal variation, the alternative sleep classifier 135 has been trained for this particular individual which boosts performance considerably.

Training in batch may be slightly more accurate; however, training during the training phase furthermore allows termination of the training phase when training is sufficient, this is a considerable advantage.

In the usage phase, control logic 150 uses sleep classification to make decisions about switching functions of controlled device 170 on or off. For example, control logic 150 may be configured with a first switching period, e.g., comprising a start time and an end time;

a set of particular sleep stages, e.g., {N1, N2, N3, N4} to indicate any sleep, e.g., {N3, N4} to indicate deep or REM sleep, e.g., {N1, N2} to indicate light sleep etc.;

a function of controlled device 170; and an indication whether the function is to be turned on or off.

If such a degree of configurability is not desired, some may be removed, say the set of sleep stages may be fixed to an indication of any sleep, etc. In the usage phase, EEG sensor 120 may be unplugged from switch 110 if this is supported by switch 110. In the training phase, control logic 150 may use classification of EEG sleep classifier 125 instead of alternative sleep classifier 135.

Typically, the switch 110 and optionally device 170 each comprise a microprocessor (not shown) which executes appropriate software stored at switch 110 and optionally device 170, e.g., that the software may have been downloaded and stored in a corresponding memory, e.g., RAM or Flash (not shown), and/or placed in ROM code. Note that part or all of switch 110 may be implemented in hardware, e.g., using integrated circuits.

Alternative sensor 130 may be a sensor to obtain a measure of gross body movements, although this is not a cardio/respiratory feature, it is a modality that may be recorded together with ECG. It is very useful to distinguish between "sleep" (any of the sleep stages) and "wake" but much less useful to distinguish between different sleep stages, for example, between N3 ("deep sleep") and REM sleep. Alternative sensor 130 may measure variations in the (heart) beat-to-beat intervals (or 'heart rate variability'). The latter are highly dependent on the activity of the sympathetic and parasympathetic nervous systems. For example, when sympathetic activity increases and/or parasympathetic activity decreases, these variations will be reduced. On the other hand, it is known that during REM sleep, there is an increase in the sympathetic activity to a level compared to (or sometimes higher than) wakefulness, and especially when compared with non-REM sleep. So certain properties of the heart rate variability, such as the high frequency power components (e.g., 0.15 to 0.40 Hz), are very discriminating between REM and non-REM sleep but much less discriminating between REM and "wake" states. Combining different sensors, e.g., a sensor for gross body movements and a sensor for heart rate variability, together increases the accuracy to detect sleep stages without EEG data.

The inventors found that the discriminating power of certain features is subject dependent. This is a consequence of the differences in physiology (including the possible existence of a certain medical condition) and behavior. For example:

Consider a person that while lying in bed, awake, does not move his/her body very much. In that case, gross body movements might be less discriminating than for a person who moves more when awake.

Heart rate variability heavily depends on age. A younger person will have higher heart rate variability than an older person. So it is only natural that for the younger person, features based on heart rate variability will discriminate better between REM (or wake) and non-REM sleep states than for an older person.

The machine learning system may compute the values of these features and/or other features for a given subject, on the one hand, and on the other hand, having access to (estimated) sleep stages for that person. Statistical methods (e.g., standardized mean difference, Mahalanobis distance, etc.) may be used to determine the degree to which a certain feature (or combination of features) discriminates well (or not) between these stages.

Figure 2:
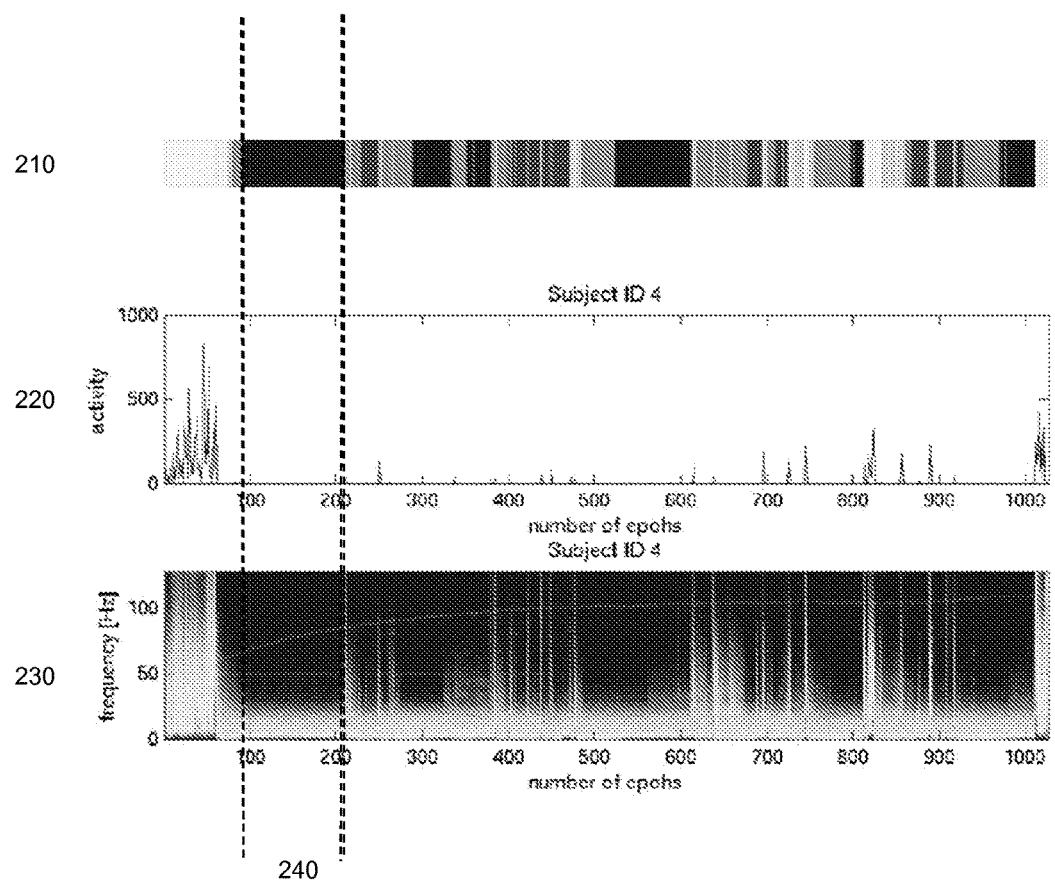
FIG. 2 shows EEG data, sleep classification data, and body activity data.

FIG. 2 illustrates the training phase. FIG. 2 shows EEG data 230, here in the form of an EEG frequency spectrum. Indeed EEG sleep classifier 125 may perform such processing as is necessary for its classification, e.g., frequency analysis. The EEG data is a facial PSG signal, showing brain activity captured as the electrical potential difference between a mastoid electrode and point above the eye (same side of the face).

FIG. 2 shows the body data of alternative sensor 130. In this case a typical RHA signal: wrist actigraphy 220. Different or additional data may be recorded; say respiration rate could have been obtained, say from a pressure sensor, or from a sensor directly attached, to the chest, e.g., a chest band, etc.

The signals in FIG. 2 are aligned, i.e., the hypnogram is aligned with wrist autography and brain power spectrum signals visualization. Data which is immediately vertically above each other, e.g., data 220 and 230, were sensed at the same time. Note that the data has been divided over epochs, here of 30 seconds each, as may be convenient, other divisions are possible. EEG sleep classifier 125 has classified EEG data 230. In FIG. 2, the sleep classification 210 has been indicated with color codes. Again, data which is vertically above each other is at the same time. Note for example, that in time period 240, EEG data 230 shows clear slow wave activity, which has been classified in the color codes 210 as deep sleep. Machine learning system 140 may use data 210 and 220 as training data, discarding EEG data 230. Note that sleep classification data 210 may be simplified if the set of sleep stages is known in the training phase, for example, if switch 110 need only depend on the presence or absence of sleep, then sleep classification data 210 may be reduced to sleep or not.

From the image, we can see that the deep sleep region marked in FIG. 2 at 240 is well manifested in slow wave brain activity. At the same moment, wrist actigraphy is steadily zero. For this individual, deep sleep classification is strongly correlated with low actigraphy. This seems to imply that actigraphy could be used to, e.g., identify deep sleep episodes. While that feature can be, in fact, sensitive to the identification of deep sleep, it's specificity in that regard varies significantly per subject. For example, the strong correlation between low actigraphy and deep sleep classification shown in FIG. 2 need not be the same for every individual, in particular, the correlation may be different. Consider, as an example, subjects who lie very still before falling asleep (e.g., because they are reading a book). In that case the actigraphy will also be very low and will make the distinction between wake and deep sleep very difficult. If, on the other hand, the subject moves significantly before falling asleep, actigraphy will provide very good discrimination between wake and deep sleep. Accuracy may be improved by adding more (RHA) sensors and/or features that are also discriminative between, e.g., wake and sleep or between sleep stages. Note that a sensor/feature that is discriminative for one subject may not be or less so for another; this need not be a problem in practice since the machine learning system will pick up the features that are discriminative for this individual.

Thus, an obtrusive contact-based brain activity measuring device (e.g., based on electrodes which could be easily placed on the user's face) based on which, after one or multiple nights recording an automatic classifier would perform sleep stage classification. Simultaneously, more convenient and unobtrusive contactless sensors would record RHA signals from that user during those same nights. These sleep stages would then be associated with characteristics of the RHA signals measured for that user and a new classifier could be built based on those characteristics. In subsequent nights, the user would no longer require the contact-based measurements of brain activity but only the monitoring of the RHA signals: the new classifier would use these signals only to automatically classify the sleep stages.

In an embodiment, the control logic is not only configured to control the device, e.g., by sending technical control data to the device instructing the device to switch functionality, e.g., from one function to another, on or off, etc; but also to record information relating to the sleep, e.g., the sleep stages classified based on the alternative or EEG sleep classifier. In this way, said sleep information may be shown to the user in the morning or archive for further follow-up or diagnosis.

Figure 3:
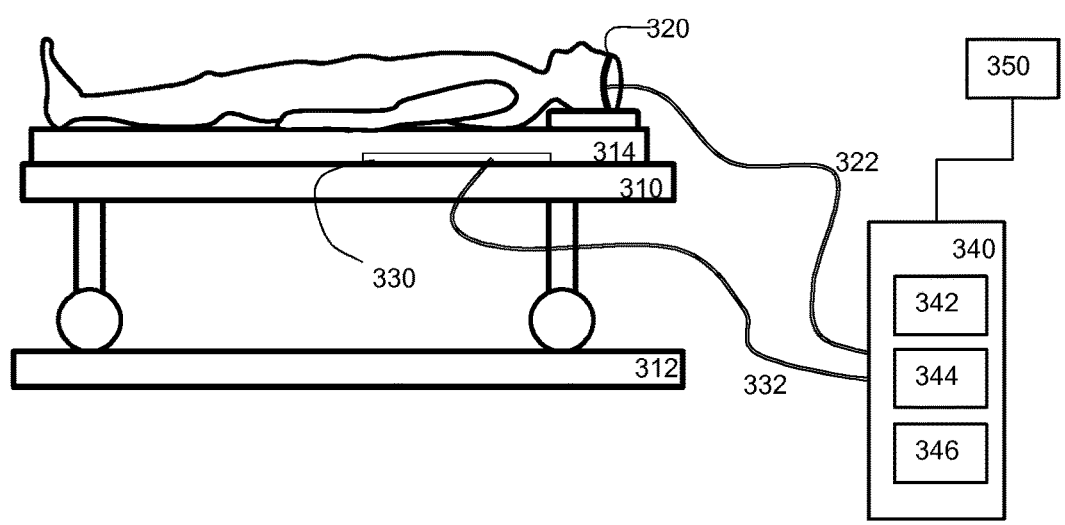
FIG. 3 illustrates a sleep dependent alarm clock.

FIG. 3 illustrates a sleep dependent alarm clock 300. FIG. 3 shows the configuration during the training phase.

Shown is a bed 310 with a mattress 314 standing on a floor 312. On the bed lies a human. Attached to the scalp of the human is an EEG sensor 320, in this cased attached with a head band, alternatives include a skull cap, glue, and the like. Note that this human is in the privacy of his own home, there is no need for him/her to go to a sleep lab. EEG sensor 320 is attached to a switch 340, in this case with an EEG sensor cable 322, the connection could also be wireless. Switch 340 is of the same basic design as switch 110. Also attached to switch 340 is a pressure mat 330 with a pressure mat cable 332, also this connection could be wireless. Pressure mat 330 is placed underneath mattress 314. It is also possible to integrate the pressure sensor in the mattress. This will increase the sensitivity of the pressure signal, which is especially advantageous to derive a cardiogram from the pressure data. Other pressure sensors than pressure mats may be used, e.g., pressure sensors incorporated in the mattress, e.g., optical sensors.

This switch 340 has been implemented using a processor 342 and a memory 344. The memory is preferably non-volatile, and may be used to store software for execution on processor 342 to implement the functions of switch 340. Switch 340 controls a device, namely, a buzzer 350. Buzzer 350 is configured to wake the human, when this function is turned on by switch 340. Note that buzzer 350 and switch 340 may well be integrated in a single device. For the alarm clock embodiment, switch 340 comprises a clock 346. For some other applications than waking at a particular time, a clock is not needed.

Switch 340 as shown is in the training phase. Switch 340 records pressure information from body sensor 330 and EEG data from EEG sensor 320. The EEG data is classified into sleep classification stages by EEG classification software placed in memory 344. When the training phase is finished, EEG sensor 320 is no longer used by the human, and may even be disconnected from switch 340. Machine learning software uses the data received from pressure mat 330 and the sleep classification to train an alternative sleep classifier to classify the body data according to the same sleep classification system used by the EEG sleep classifier.

Control software of switch 340 may be programmed to wake the human in an appropriate manner, for example: between 6:00 and 6:30 turn on buzzer 350 if the body data is classified by the alternative sleep classifier as light sleep, say N1 or (N1 and N2), between 6:30 and 6:35 turn on the buzzer regardless of classification of the alternative sleep classifier. Switch 340 may conveniently be configured with a button to turn off the function, say turn off buzzer 350.

In an especially convenient embodiment, buzzer 350 is configured for placement in the ear. For example, switch 340 may be configured with two or more switches, the two switches may share some components, e.g., the clock, the EEG sleep classifier itself, optionally only a single EEG sensor may be used. Sensor 320 would then be connectable to the two or more switches in turn. This means, e.g., that switch 340 could classify the sleep stage of each of the two people in a couple, for each one of them an ideal waking moment based on sleep classification may be detected. Because the buzzer is worn in the ear, only the correct person is woken. Preferably, the buzzer is then connected wirelessly to switch 340. An ear-worn buzzer may even be integrated with a switch and body sensor, in that case there is no need for a wireless connection, each person would have his own switch. For example such sensors for such bodily functions as heartbeat, body temperature, and actiography may be configured for placement in the ear as an ear piece.

A sleep stage dependent alarm clock may combine a sensor for heart, movement, and/or respiratory measurement device. 'Out of the box' the system is trained to classify sleep stages based on the measured brain wave data. During a training phase, the system is trained with the classified sleep stages to classify sleep stages using only the data obtained from the heart/movement/respiratory measurement device or devices. In a usage phase, the system does not use a head electrode, only the simpler system, i.e., the heart/movement/respiratory measurement device or devices. The alarm clock uses the classified sleep stage to wake you up in the 'right sleep stage moment' so that you feel refreshed.

Other applications of switch 110 than sleep stage dependent alarm clock 340 include sleep dependent switching off of equipment, such as home entertainment systems, and sleep dependent switching on of a house alarm system.

Figure 4:
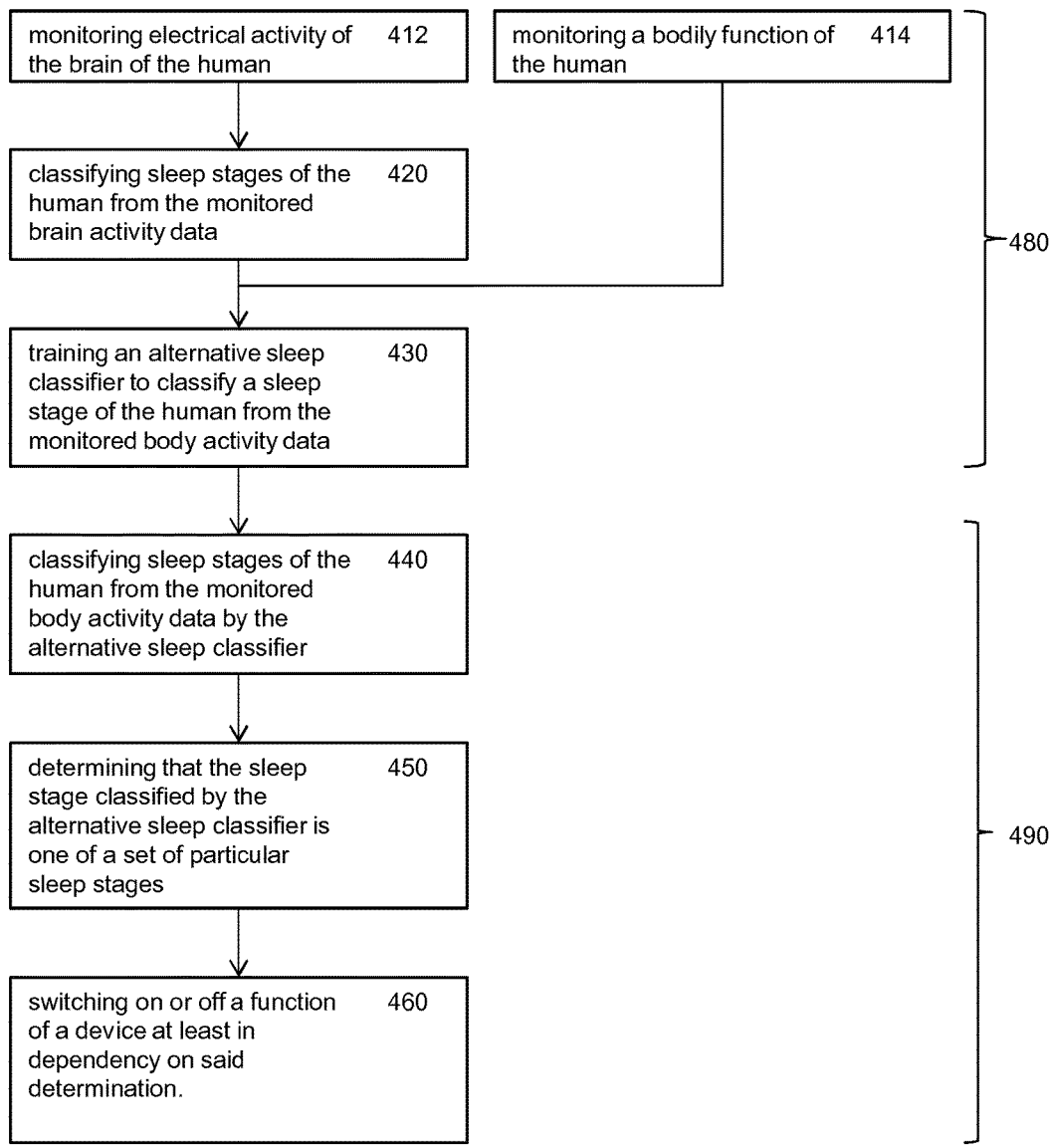
FIG. 4 illustrates, in a flowchart, a method for sleep-dependent controlling of a device.

FIG. 4 illustrates, in a flowchart, a method 400 for controlling device 170 by switching on or off a function of the device at least in dependency on a sleep stage of a human. The flowchart shows a training phase 480 and a usage phase 490. The training phase comprises a step 412, monitoring electrical activity of the brain of the human, e.g., with an EEG sensor, and a step 414, monitoring a bodily function of the human. Note that steps 412 and step 414 are concurrent or at least overlap considerably. In step 420 of the training phase, the monitored brain activity data, i.e., the EEG data, is classified into sleep stages, e.g., using an EEG sleep classifier. Finally, the sleep classification together with the monitored body activity data is used to train an alternative sleep classifier to classify a sleep stage, e.g., using a machine learning system. At the end of the training phase, the alternative sleep classifier is able to classify body activity data according to sleep classification system considerably better than it would have been when trained on data for a different human, or even an 'average' human.

The usage phase 490 comprises step 440, classifying sleep stages of the human from the monitored body activity data by the alternative sleep classifier. In step 450, it is determined that the sleep stage classified by the alternative sleep classifier is one of a set of particular sleep stages. If so then in step 460 a function of a device is switched on or off at least in dependency on said determination. There may be other types of input considered, e.g., time information from a clock, or information obtained from an external information providing system.

Many different ways of executing the method are possible, as will be apparent to a person skilled in the art. For example, the order of the steps can be varied or some steps may be executed in parallel. Moreover, in between steps other method steps may be inserted. The inserted steps may represent refinements of the method such as described herein, or may be unrelated to the method. For example, steps 412 and 414 are executed, at least partially, in parallel. Moreover, a given step may not have finished completely before a next step is started.

A method according to the invention may be executed using software, which comprises instructions for causing a processor system to perform method 400. Software may only include those steps taken by a particular sub-entity of the system. The software may be stored in a suitable storage medium, such as a hard disk, a floppy, a memory etc. The software may be sent as a signal along a wire, or wireless, or using a data network, e.g., the Internet. The software may be made available for download and/or for remote usage on a server.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. An embodiment relating to a computer program product comprises computer executable instructions corresponding to each of the processing steps of at least one of the methods set forth. These instructions may be subdivided into sub-routines and/or be stored in one or more files that may be linked statically or dynamically. Another embodiment relating to a computer program product comprises computer executable instructions corresponding to each of the means of at least one of the systems and/or products set forth.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A burglar alarm comprising:
an intrusion sensor for detecting an intrusion of a burglar;
a device configured to raise an alarm in response to the intrusion sensor detecting an intrusion; and an electronic switch for controlling the device by switching a function of the device at least in dependency on a sleep stage of a human,
wherein the electronic switch comprises:
an electroencephalogram (EEG) sensor configured to monitor electrical activity of a brain of the human;
an EEG data interface configured to receive brain activity data from the EEG sensor during a training phase;
an EEG sleep classifier configured to classify sleep stages of the human from the received brain activity data;
an alternative sensor configured to monitor a bodily function of the human, the alternative sensor being different from the EEG sensor;
a body data interface configured to receive body activity data from the alternative sensor both during the training phase and during a subsequent usage phase;
an alternative sleep classifier and a machine learning system, the machine learning system being configured to train the alternative sleep classifier to classify a sleep stage of the human from the received body activity data, the machine learning system using sleep stages classified by the EEG sleep classifier and concurrent body activity data received from the alternative sensor as training data, wherein, in the usage phase, the device is controlled in dependency on sleep stages of the human classified by the alternative sleep classifier;
control logic configured to at least determine that the classified sleep stage is one of a set of particular sleep stages and to switch a function of the device at least in dependency on said determination;
a statistical unit configured to
determine a statistical measure of the received body activity data during the training phase and store it as a reference measure, and to
determine the statistical measure of the received body activity data during the usage phase; and
a drift detection unit configured to detect a drift of the statistical measure determined during the usage phase and the reference measure, and upon detecting the drift signaling a user for recalibration of the alternative sleep classifier,
wherein the control logic is configured to switch-on the device configured to raise an alarm.

2. The burglar alarm as claimed in claim 1, wherein said electronic switch further comprises a clock configured to indicate a current time, the switch being configurable with a first switching time-period, the control logic being configured to switch the function when both:
a current time indicated by the clock is in the first switching period, and
the classified sleep stage is one of the set of particular sleep stages.

3. The burglar alarm as claimed in claim 2, wherein the control logic is configured to switch the function when a current time indicated by the clock is at the end of the first switching period regardless of the classified sleep stage.

4. The burglar alarm as claimed in claim 1, wherein the control logic is configured to defer switching until the classified sleep stage has remained in the set of particular sleep stages for a particular time period.

5. The burglar alarm as claimed in claim 1, wherein
the EEG sensor is configured to monitor when placed in close proximity or direct contact to the head of the human, and
the alternative sensor is configured to monitor without direct contact with the human.

6. The burglar alarm as claimed in claim 1, wherein the alternative sensor is configured to monitor at least one of respiration, heart and actigraph.

7. The burglar alarm as claimed in claim 1, wherein the alternative sensor comprises a pressure sensor for positioning in or under a mattress.

8. An alarm clock comprising:
the burglar alarm as claimed in claim 1; and
a device configured to wake the human using audio and/or visual stimuli, wherein
the electronic switch is configurable with a first switching time period, and
the control logic is configured to switch-on the device to generate audio and/or video stimuli thereby waking the human.

9. The alarm clock as in claim 8, wherein at least the device configured to wake the human is arranged for wearing in a human ear.

* * * * *